US00PP13278P3

(12) United States Plant Patent
Olesen et al.

(10) Patent No.: US PP13,278 P3
(45) Date of Patent: Nov. 26, 2002

(54) COMPACT FLORIBUNDA ROSE PLANT NAMED 'POULAC003'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/776,158

(22) Filed: Feb. 2, 2001

(65) Prior Publication Data

US 2002/0148014 P1 Oct. 10, 2002

(51) Int. Cl.[7] ..... A01H 5/00

(52) U.S. Cl. ..... Plt./145

(58) Field of Search ..... Plt./145, 141, 102

*Primary Examiner*—Bruce R. Campell
*Assistant Examiner*—June Hwu

(57) ABSTRACT

A new compact floribunda rose which has abundant, yellow flowers and attractive foliage. This new and distinct variety has shown to be uniform and stable in the resulting generations from asexual propagation.

1 Drawing Sheet

BOTANICAL CLASSIFICATION

*Rosa hybrida* 'POULac003'.

SUMMARY OF THE INVENTION

The present invention constitutes a new and distinct variety of a compact floribunda rose plant which originated from a controlled crossing between two unnamed, non-patented seedlings created by the same inventor. The two parents were crossed during the summer of 1995 and the resulting seeds were planted in a controlled environment in Fredensborg, Denmark. The new variety is named 'POULac003'.

The new rose may be distinguished from its seed parent, an unnamed seedling (non-patented), by the following combination of characteristics:

1. 'POULac003' has deep yellow flowers, while the seed parent has soft yellow flowers.
2. 'POULac003' is lower, compact and more bushy in growth when compared to the seed parent.

The new variety may be distinguished from its pollen parent (non-patented), an unnamed seedling by the following combination of characteristics:

1. 'POULac003' flowers are a deep yellow flower color, whereas the pollen parent has soft yellow flowers.
2. 'POULac003' when grown as a pot plant has a longer shelf life than the pollen parent.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Disease resistance.
4. Suitable characteristics for a pot plant cultivation.

This combination of qualities is not present in previously available commercial cultivars of this type and distinguish 'POULac003' from all other varieties of which we are aware.

As part of their rose development program, L. Pernille Olesen and Mogens N. Olesen germinated the seeds from the aforementioned hybridization during winter 1995 and conducted evaluations on the resulting seedlings in a controlled environment in Fredensborg, Denmark.

'POULac003' was selected in the spring 1996 by the inventors as a single plant from the progeny of the aforementioned hybridization. Asexual reproduction of 'POULac003' by traditional budding and rooted cuttings was first done by L. Pernille and Mogens N. Olesen in their nursery in Fredensborg, Denmark in July 1996. This initial and other subsequent asexual propagations conducted in controlled environments have demonstrated that the characteristics of 'POULac003' are true to type and are transmitted from one generation to the next.

BRIEF DESCRIPTION OF THE DRAWING

The accompanying color illustration shows as true as is reasonably possible to obtain in color photographs of this type the variety rose 'POULac003'. Specifically illustrated in SHEET 1 include:

1. Rose plant exhibiting foliage, leaves, and leaflets.

2. Flower bud, partially opened bud, and open bloom;

3. General plant growth and habit.

DETAILED DESCRIPTION OF THE VARIETY

The following is a description of 'POULac003' as observed in its growth in Jackson County, Oreg., on plants aged eighteen weeks. Color references are made using The Royal Horticultural Society (London, England) Colour Chart, 1995, except where common terms of color are used.

For a comparison, several physical characteristics of the rose variety 'POULsiana', a rose variety from the same inventors described and illustrated in U.S. Plant Pat. No. 11,638 issued Nov. 21, 2000, are compared to 'POULac003' in Chart 1.

CHART 1

| | 'POULac003' | 'POULsiana' |
|---|---|---|
| Color of open flower, outer side, middle zone. | Yellow Group 10B | Yellow Group 7B |
| Petalage | 25–28 | 15–20 |
| Flower size | 8–10 cm | 5–6 cm |

Classification:
*Commercial.*—Compact floribunda.
Parents:
*Seed parent.*—Unnamed seedling.
*Pollen parent.*—Unnamed seedling.

FLOWER AND FLOWER BUD

Blooming habit: Continuous.
Flower bud:
*Size.*—25 to 35 mm in length from base of receptacle to end of bud.
*Bud form.*—Pointed ovoid.
*Bud color.*—As sepals unfold, Yellow Group 10B; Yellow Group 11B at ¼ opening.
*Sepals.*—Length: 15 to 35 mm. Width: 8 to 9. Color: Upper surface is Yellow-Green Group 146A at margins and Yellow-Green Group 146D in interior. Lower surface is Yellow-Green Group 146B. Appendages: Strong foliaceous appendages on 4 of the five to six sepals. Pubescence: Moderate.
*Stipitate glands.*—Many stipitate glands on sepal margins.
*Receptacle.*—Surface: Smooth. Shape: Funnel-shaped. Size: 6 mm (h)×8 mm (w). Color: Green Group 143C.
*Peduncle.*—Surface: Many stipitate glands present. Length: 55 to 60 mm. Color: Yellow-Green Group 145A. Strength: Somewhat strong. Anthocyanin: Greyed-Orange Group 176A.
*Borne.*—Singularly.
Flower bloom:
*Fragrance.*—Very faint.
*Duration.*—As a pot plant, flowers last from 12 to 15 days.
*Persistence.*—Petals fall cleanly from the plant.
*Size.*—Medium. Average flower diameter is between 70 to 80 mm when open.
*Form.*—Shape of flower when viewed from the side: Upon opening, upper part: Flat. Upon opening, lower part: Flat. After opening, upper part: Flattened convex. After opening, lower part: Flat.
*Petalage.*—Double. Average range: 25 to 28 petals, with 3 to 5 petaloids.
Color:
*Upon opening, petals.*—Outermost petals: Upper surface: Yellow Group 10A. Lower surface: Yellow Group 11A. Innermost petals: Upper surface: Yellow Group 11A. Lower surface: Yellow Group 11A.
*Upon opening, basal petal spots.*—Upper surface: Yellow Group 8B. Lower surface: None noted.
*After opening, petals.*—Outermost petals: Upper surface: Yellow Group 11B. Lower surface: Yellow Group 11B. Innermost petals: Upper surface: Yellow Group 11B. Lower surface: Yellow Group 11B.
*After opening, basal petal spots.*—Upper surface: Yellow Group 7D. Lower surface: None noted.
General tonality: On open flower, Yellow Group 11B. No change in the general tonality at the end of the $7^{th}$ day. Afterwards, general tonality is Yellow Group 11C.
Petals:
Size.—12 mm (l)×10 mm (w).
*Petal reflex.*—Strong.
*Shape.*—Round. Apex is rounded, base is acute.
*Petaloids.*—3 to 5. Petaloids are 25 mm long and 10 to 15 mm wide. Petaloid coloration is Yellow Group 11A on both upper and lower surfaces.
*Thickness.*—Average.
*Arrangement.*—Imbricated.
Reproductive organs:
*Filaments.*—Color: Yellow Group 12A. Length: 9 mm.
*Pistils.*—Length: 8 mm. Quantity: 35.
*Pollen.*—Color: Yellow-Orange Group 22A. Quantity: Average.
*Anthers.*—Length: 1 mm. Color: Margins are Yellow-Orange Group 22A; interior is Yellow Group 12A. Quantity: 25 to 30.
*Stigmas.*—Height: Stigmas are even in height relative to anthers. Color: Yellow-Green Group 154D.
*Styles.*—Color: Yellow-Green Group 150C, with intonations of Red-Purple Group 63C.
*Hips.*—None observed.

PLANT

Plant growth: Compact, bushy and even growth. When grown as a 15-cm pot plant, the average height of the plant is 40 cm and the average width is 60 cm.
Stems:
*Color.*—Young wood: Yellow-Green Group 146D. Older wood: Yellow-Green Group 146C.
*Thorns.*—Incidence: 10 to 12 thorns per 10 cm of stem. Size: Average length is 4 to 5 mm. Color: Greyed-Orange Group 174B. Shape: Deeply concave.
*Surface.*—Older wood: Smooth. Young wood: Smooth.
Plant foliage:
*Number of leaflets on normal leaves in middle of a stem.*—5.
*Leaf size.*—110 mm (l) by 80 mm (w).
*Quantity.*—Average.
*Glossiness.*—Upper side weak glossiness.
*Color.*—Mature foliage: Upper Leaflet Surface: Green Group 137A. Lower Leaflet Surface: Green Group 138B. Juvenile foliage: Upper Leaflet Surface: Green Group 137A. Lower Leaflet Surface: Green Group 138B. Anthocyanin intonation: Greyed-Red Group 178A.
Plant leaflets:
*Stipule.*—Length: 6 mm. Color: Green Group 143A in margins; Yellow-Green Group 145B in interior. Anthocyanin: Greyed-Red Group 178A.
*Petiole.*—Length: 12 to 15 mm. Color: Green Group 143A. Underneath: Stipitate glands and occasionally a single, small thorn. Margins: Stipitate glands present. Anthocyanin: Greyed-Red Group 178A.
*Rachis.*—Color: Green Group 143A. Underneath: Stipitate glands and occasionally a single, small thorn. Margins: Stipitate glands present. Anthocyanin: Greyed-Red Group 178A.
*Leaflet.*—Edge: Serrate. Shape: Ovate. Surface: Moderately glossy. Texture: Leathery. Arrangement: Odd pinnate. Venation: Reticulate.

Disease resistance: Above average resistance to mildew, rust, black spot, and Botrytis under normal growing conditions in Fredensborg, Denmark and Hannover, Germany.

Cold hardiness: The variety 'POULac003' has been found to be cold hardy in Fredensborg, Denmark; and Hannover, Germany.

We claim:

1. A new and distinct variety of rose plant of the compact floribunda rose class, substantially as herein illustrated and described as a distinct and novel rose variety due to its abundant yellow flowers, disease resistance, and extended period of bloom.

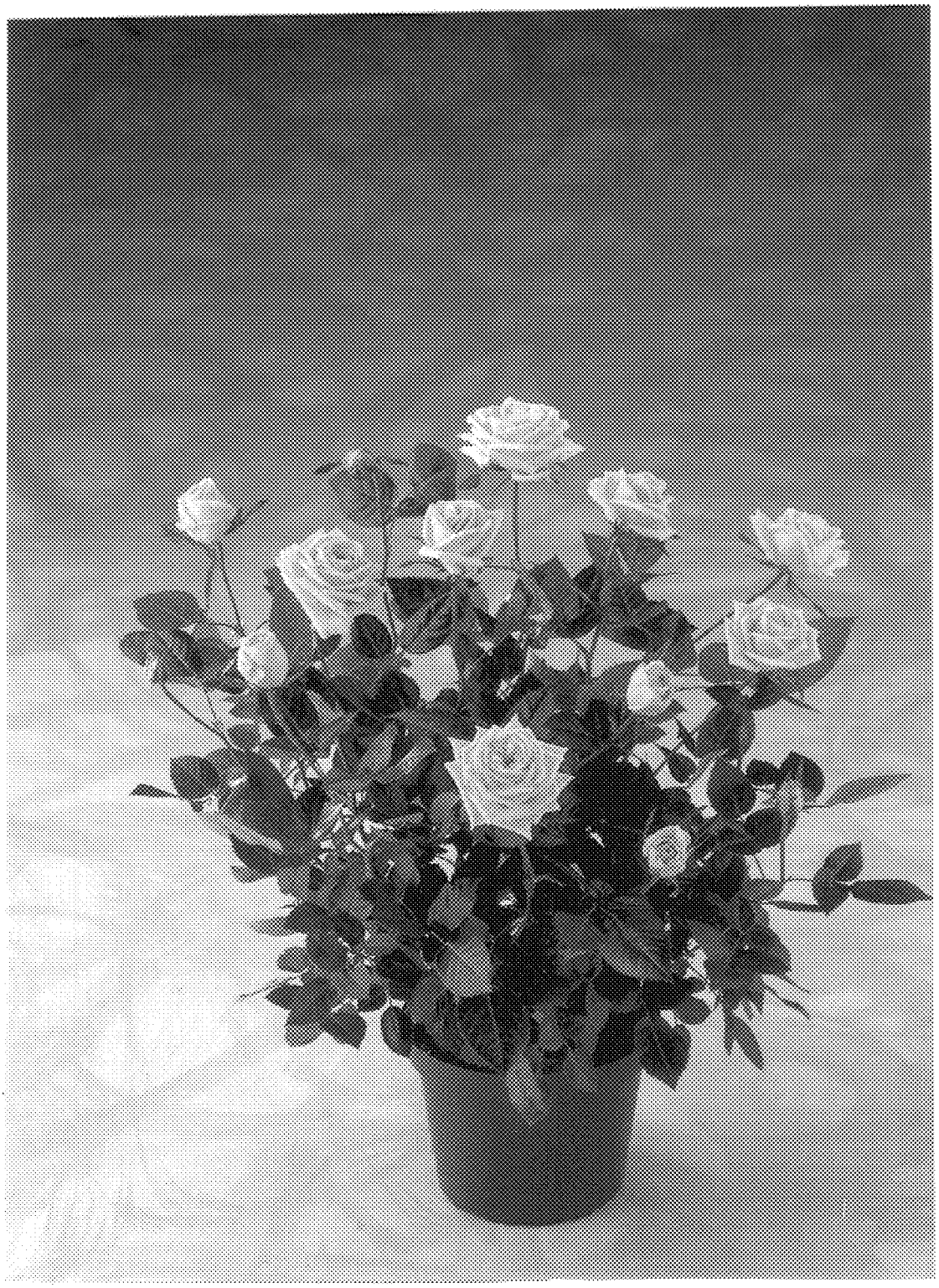

* * * * *